United States Patent [19]

Elsnau

[11] 4,049,792
[45] Sept. 20, 1977

[54] ANTIPERSPIRANT STICK
[75] Inventor: Walter Hugh Elsnau, Cincinnati, Ohio
[73] Assignee: The Procter & Gamble Company, Cincinnati, Ohio
[21] Appl. No.: 632,128
[22] Filed: Nov. 14, 1975

Related U.S. Application Data
[63] Continuation of Ser. No. 373,820, June 26, 1973, abandoned.
[51] Int. Cl.$^2$ ............................................. A61K 7/34
[52] U.S. Cl. ............................... 424/66; 424/DIG. 5; 424/68
[58] Field of Search ..................... 424/66, DIG. 5, 68
[56] References Cited
U.S. PATENT DOCUMENTS

| 1,984,669 | 12/1934 | Taub | 424/65 |
|---|---|---|---|
| 2,087,161 | 7/1937 | Moore | 424/68 X |
| 2,566,722 | 9/1951 | Friedberg | 424/DIG. 5 |
| 2,865,859 | 12/1958 | Lubowe | 424/66 X |
| 2,889,253 | 6/1959 | Berger et al. | 424/170 X |
| 2,890,152 | 6/1959 | Babcock, Jr. et al. | 424/68 X |
| 2,893,918 | 7/1959 | Abramson | 424/DIG. 5 |
| 3,098,795 | 7/1964 | Kreps | 424/DIG. 5 |
| 3,194,736 | 7/1965 | Braun et al. | 424/DIG. 5 |
| 3,255,082 | 7/1966 | Barton | 424/DIG. 5 |
| 3,259,545 | 7/1966 | Teller | 424/66 |
| 3,325,367 | 6/1967 | Wiechowski | 424/66 |

OTHER PUBLICATIONS

American Perfumer & Cosmetics, 1963, vol. 78 p. 50.
Drug & Cosmetic Industry, Nov. 1968, p. 80
Drug & Cosmetic Industry, Nov. 1950, vol. 67, No. 5 p. 687.
Household & Personal Products Formulary, Sept. 1972.

Primary Examiner—Dale R. Ore
Attorney, Agent, or Firm—Ronald L. Hofer; George W. Allen; Douglas C. Mohl

[57] ABSTRACT

A very effective antiperspirant composition in the form of a stick comprising from abouyt 1% to about 20% of a water-insoluble wax, from about 20% to about 50% of an essentially water-insoluble, but water-dispersible, liquid emollient, and from about 30% to about 60% of an activealuminum or zirconium astringent antiperspirant salt in the form of finely divided particles, said composition being essentially water-insoluble with the exception of the active particles.

7 Claims, No Drawings

ANTIPERSPIRANT STICK

CROSS REFERENCE TO RELATED APPLICATION

This application is a continuation of the copending application of Walter Hugh Elsnau having Ser. No. 373,820, filed June 26, 1973, now abandoned.

BACKGROUND OF THE INVENTION

1. Field of the Invention

This invention relates to antiperspirant compositions in the form of a stick.

2. Prior Art

The use of stick antiperspirant compositions is well known. However, most of the stick antiperspirant compositions known heretofore have included a relatively insoluble soap, see for example, Taub; U.S. Pat. No. 1,984,669; issued Dec. 18, 1934 and more typically, a soap gel, see for example, Teller; U.S. Pat. No. 2,732,327; issued Jan. 24, 1956. Almost all of the prior art stick antiperspirant compositions contain either water or large amounts of water-soluble materials. For example, Moore; U.S. Pat. No. 2,087,162; issued July 13, 1937 discloses a composition containing large amounts of isopropyl alcohol. Most prior art antiperspirant stick compositions also fail to have sufficient active present, for example, the formulas shown in the Formulary section of *Household and Personal Products Industry*, September 1972.

Similar compositions which do not contain water-soluble compounds in large amounts have been disclosed, but these have not been antiperspirant compositions. See, e.g., Mohrlok; U.S. Pat. No. 3,641,239; issued Feb. 8, 1972, which relates to a lipstick, rouge, mascara or styptic crayon containing a silicone wax.

The stick antiperspirant prior art compositions, although effective, do not suggest the compositions of this invention which are surprisingly more effective than the compositions of the prior art. Further, the compositions of the present invention are more cosmetically appealing than prior art compositions. Even further, the efficacy of compositions of the present invention is longer-lasting than that of prior art compositions. Still further, the stick antiperspirant compositions of the present invention are stable, offer safety advantages over aerosol antiperspirant products, are substantially non-irritating to the skin, and do not require a complicated package for dispensing and preventing "dry-out", giving the present compositions advantages over other antiperspirant compositions.

Unless indicated otherwise, all percentages hereinafter are percentages by weight.

SUMMARY OF THE INVENTION

This invention relates to a very effective antiperspirant stick composition comprising from about 1% to about 20% of a water-insoluble wax having a melting point of from about 150° F. to about 215° F.; from about 20% to about 50% of an essentially water-insoluble, but water-dispersible, liquid emollient; and from about 30% to about 60% of a relatively water-soluble aluminum or zirconium astringent antiperspirant salt in finely divided particulate form dispersed in said composition. The composition may optionally contain from 0% to about 25% of a relatively water-insoluble waxy material having a melting point of from about 100° F. to about 150° F., such as a fatty acid or a fatty alcohol and from 0% to about 10% of a water-insoluble, inert filler material in the form of finely divided particles dispersed in said composition.

DESCRIPTION OF THE INVENTION

Applicant has surprisingly discovered a very effective, non-irritating, cosmetically attractive antiperspirant composition in the form of a stick comprising a wax, a liquid emollient, and an astringent aluminum or zirconium salt. Optionally, the present compositions may contain a waxy material having a melting point of from about 100° F. to about 150° F. and/or an inert filler material. These ingredients are more specifically described below.

While applicant does not wish to be bound by any theory, it is believed that the structure of a composition of the present invention is highly important in determining both the cosmetic attractiveness and antiperspirant efficacy of the stick antiperspirant. A stick antiperspirant composition of the present invention is essentially anhydrous, containing no volatile ingredients. Thus, a composition of the present invention does not impart a wet impression to the user. Further, the antiperspirant active ingredient is dispersed throughout the product at a highly effective concentration. When the composition is applied to the skin, the other required ingredients of the composition hold the active to the skin. It has been surprisingly discovered that the level of antiperspirant active in the composition is critical to improved efficacy as an antiperspirant. It was surprisingly discovered that merely adding more of a composition containing a lower concentration of antiperspirant active does not give equivalent performance to a composition of the present invention which employs the active at a higher concentration.

It is further believed that the present compositions comprising essentially water-insoluble materials and a water-soluble aluminum or zirconium salt form an insoluble film on the skin while holding a soluble active ingredient against the skin to help prevent perspiration resulting in an antiperspirant product which resists washing away by sweat but is easily washed away by a soap solution. Thus, the present compositions are effective for long periods of time.

The Water-Insoluble Wax

A high melting point water-insoluble wax provides the basic structure of the composition. Suitable waxes are water-insoluble waxes having a melting point of from about 150° F. to about 215° F. and are hereinafter referred to as high melting point waxes. Examples of suitable waxes are beeswax, spermaceti, carnauba, bayberry, candelilla, montan, ozokerite, ceresin, paraffin, synthetic waxes such as Fisher-Tropsh waxes, and microcrystalline wax. Preferred waxes are ceresin, ozokerite, white beeswax and synthetic waxes. It is speculated that the high melting point wax provides a structure which can be sheared when applied to the skin, thereby exposing the active particles described hereinafter to the skin. The present compositions may contain from about 1% to about 20% of this wax. The preferred amount of high melting point wax is from about 5% to about 15%, most preferably from about 6% to about 10%. Higher levels of wax lead to lower wear rates, and lower levels of wax tend to give higher wear rates and a softer, less desirable structure which feels sticky to the user and does not provide adequate shearing action in use.

The Liquid Emollient

The liquid emollient is an essential ingredient in the preparation of the antiperspirant stick of this invention. Such emollients are in liquid form at room temperature (about 72° F). It has been discovered that water-soluble emollients are not desirable components of a stick antiperspirant composition. However, the liquid emollients of this invention are water-dispersible in the presence of a surfactant, e.g., soap, which is desirable in that it permits the removal of the antiperspirant composition by taking a shower or a bath. Any liquid, non-toxic, non-irritating organic material having a solubility in water of from about 0.0005% to about 1.0% at 72° F. can be used. Preferred emollients include fatty acid and fatty alcohol esters, e.g., isopropyl myristate, isopropyl palmitate, cetyl acetate, cetyl propionate, etc. Other preferred emollients are relatively water-insoluble ethers and alcohols such as polypropylene glycol, the condensation product of one or two moles of ethylene oxide with behenyl alcohol, etc. Especially preferred emollients include ispropyl myristate, isopropyl palmitate and Fluid AP, a commercially available emollient comprising the condensation product of about fourteen moles of propylene oxide with one mole of butyl alcohol.

The present compositions may contain from about 20% to about 50% of a liquid emollient. The preferred amount of liquid emollient is from about 30% to about 50%, most preferably from about 35% to about 45%.

The Antiperspirant Active

The present compositions contain, as an essential ingredient, an antiperspirant active. Any aluminum or zirconium astringent antiperspirant salt in the form of impalpable particles may be employed. Such salts are well known in the antiperspirant art.

Preferred antiperspirant actives include impalpable aluminum chlorhydroxide and aluminum hydroxybromide as well as the antiperspirant actives disclosed in the copending application of Raymond E. Bolich, Jr., having Ser. No. 59,690, filed July 30, 1970, and in U.S. Pat. No. 3,792,068, issued Feb. 12, 1974 to Luedders et al.

This Luedders et al patent discloses a complex of aluminium, zirconium and amino acid formed by
A. Co-dissolving in water
  1. one part $Al_2(OH)_{6-m}X_m$, wherein X is an anion selected from the group consisting of chloride, bromide and iodide and $m$ is a number from about 0.8 to about 1.2;
  2. n parts ZrY wherein Y is an anion selected from the group consisting of —O(OH)Cl and $OCl_2$, and where n has a value of from about 0.16 to about 1.2;
  3. p parts neutral amino acid selected from the group consisting of glycine, dl-tryptophane, dl-$\beta$-phenylalanine, dl-valine, dl-methionine and $\beta$-alanine, and where p has a value of from about 0.06 to about 0.53;
B. Co-drying the resultant mixture at a temperature of from about 100° C. to about 230° C. to a moisture level of from about 0.5% to about 15% by weight; and
C. Comminuting the resultant dried inorganic-organic antiperspirant complex into the form of and impalpable powder.

The preferred aluminium compound for preparation of the Luedders et al complex is aluminum chlorhydroxide of the formula $Al_2(OH)_5Cl\cdot 2H_2O$. The preferred zirconium compound for preparation of the Luedders et al complex is zirconyl hydroxychloride having the formula $ZrO(OH)Cl\cdot 3H_2O$. The preferred amino acid for preparing the Luedders et al complex is glycine of the formula $CH_2(NH_2)COOH$. (Salts of such amino acids can also be employed in such antiperspirant complexes.)

Other preferred actives for use in the present invention include mixtures of aluminum chloride and aluminum hydroxychloride.

The present compositions may contain from about 30% to about 60% of an antiperspirant active ingredient. The preferred amount of antiperspirant active is from about 30% to about 50%, preferably from about 40% to about 50%. Higher levels tend to give a product which crumbles too easily and lower levels give a product which is less effective.

A Low Melting Point Wax

The present compositions may also contain, as an optional ingredient, from 0% to about 25% of a waxy material having a melting point of from about 100° F. to about 150° F. Preferred low melting point waxes are fatty acids containing from about 8 to about 20 carbon atoms, fatty alcohols containing from about 8 to about 20 carbon atoms, silicone waxes and glycerol monostearate. Especially preferred materials of this type are the $C_8$ to $C_{20}$ fatty acids and $C_8$ to $C_{20}$ fatty alcohols. The most preferred low melting point waxes are cetyl alcohol, stearyl alcohol, myristyl alcohol, lauryl alcohol and glycerol monostearate.

The preferred amount of the low melting point wax is from about 5% to about 15%, preferably from about 8% to about 12%.

The low melting point wax can be used as an adjunct to the high melting point wax to provide structure and as an emollient. The low melting point wax can also be used to adjust the feel of the stick. One skilled in the art will easily be able to make a product which feels more brittle, soft, slippery, sticky, rough, etc., by blending various suitable high melting point and low melting point waxes. The use of a silicone wax tends to cause the stick to feel more slippery to the user.

Inert Filler

In addition to the ingredients named hereinbefore, it is also optional to have in the compositions from 0% to about 10% of an inert particulate filler material such as a colloidal silica, e.g., Cab-O-Sil (Cabot Corp.), a pyrogenic silica having a particulate diameter between about 0.001 and 0.03 microns as disclosed in British Pat. No. 987,301 and British Pat. No. 1,167,173, or finely divided hydrophobic clays such as a reaction product of a clay such as Bentonite and dimethyldistearyl ammonium chloride (Bentone 34 or Bentone 38, NL Industries) as disclosed in British Pat. No. 1,167,173, or talc.

In addition to the above ingredients, it is desirable to include a perfume, stabilizing agent, pigments, coloring agent, antibacterial agents, etc., in small amounts. Examples of additional ingredients include $TiO_2$ (pigment), oil soluble dyes, and zinc phenol sulfonate (antibacterial agent). However, it is desirable that only small amounts of hydrophilic ingredients are used in addition to the active material. Preferably, less than about 5% of the composition, in addition to the active ingredients, is soluble in water.

The stick antiperspirant compositions of the present invention are prepared by heating the solid waxes and liquid emollient in a suitable container while gently stirring. When the wax or waxes are melted and mixed thoroughly with the emollient, the antiperspirant active ingredient is mixed and dispersed in the melt. The optional ingredients may then be added or the melt may be allowed to cool to a temperature above the solidification point before adding additional ingredients.

The following examples are intended to illustrate but not to limit the present invention.

EXAMPLE I

In the following example, the wax, cetyl alcohol, and propylene oxide condensates were combined in a steel vessel and heated and gently stirred until the wax and cetyl alcohol had melted and were well intermixed in each other and the propylene oxide condensates. Next, the aluminium chlorhydroxide was stirred into the composition and dispersed therein. This mixture was then allowed to cool to just above the solidification temperature at which point the perfume was stirred into the mixture which was finally poured into a mold of cylindrical shape and allowed to solidify.

| Ingredient | Percent by Weight |
| --- | --- |
| Ozokerite wax | 8.5 |
| Cetyl alcohol | 10.0 |
| Emollient (Condensation Product of about 14 moles of propylene oxide with one mole of butyl alcohol) | 37.7 |
| Aluminum chlorhydroxide | 43.0 |
| Perfume | 0.8 |
| | 100.0 |

The following examples were all prepared similarly to Example I. The waxy ingredients and emollient were first melted and intermixed at which time the antiperspirant active ingredient was added followed by the other ingredients. The mixture was then allowed to solidify.

EXAMPLE II

| Ingredient | Percent by Weight |
| --- | --- |
| Ozokerite wax | 4.0 |
| Cetyl alcohol | 9.5 |
| Fluid AP® (Propylene oxide/butyl alcohol condensate) | 39.5 |
| Aluminum chlorhydroxide | 43.5 |
| Perfume | 0.5 |
| Cab-O-Sil (grade M-5) | 3.0 |
| | 100.0 |

EXAMPLE III

| Ingredient | Percent by Weight |
| --- | --- |
| Ozokerite wax | 2.5 |
| Cetyl alcohol | 8.0 |
| Isopropyl palmitate | 40.0 |
| Zirconium hydroxychloride/aluminum chlorhydroxide/glycine complex | 45.4 |
| Perfume | 0.5 |
| Cab-O-Sil (grade M-5) | 3.6 |
| | 100.0 |

EXAMPLE IV

| Ingredient | Percent by Weight |
| --- | --- |
| Carnauba wax | 3.0 |
| Beeswax | 2.0 |
| Stearyl alcohol | 7.0 |
| Isopropyl myristate | 44.0 |
| Aluminum chlorhydroxide | 40.0 |
| Perfume | 1.0 |
| Bentone 38 | 3.0 |
| | 100.0 |

EXAMPLE V

| Ingredient | Percent by Weight |
| --- | --- |
| Beeswax | 4.0 |
| Paraffin | 12.5 |
| Isopropyl myristate | 37.0 |
| Vaseline® | 9.0 |
| Aluminum chlorhydroxide | 31.5 |
| Perfume | 0.5 |
| Cab-O-Sil (grade M-5) | 5.5 |
| | 100.0 |

EXAMPLE VI

| Ingredient | Percent by Weight |
| --- | --- |
| Ozokerite wax | 8.5 |
| Cetyl alcohol | 8.5 |
| Isopropyl palmitate | 35.0 |
| Aluminum chlorhydroxide | 43.5 |
| Perfume | 0.5 |
| Cab-O-Sil (grade M-5) | 4.0 |
| | 100.0 |

What is claimed is:

1. A stick antiperspirant composition essentially anhydrous and comprising essentially water-insoluble materials and a water-soluble antiperspirant salt, said composition comprising
   A. from about 1% to about 20% of a high melting point water-insoluble wax which has a melting point of from about 150° F. to about 215° F and which is selected from the group consisting of beeswax, spermaceti, carnauba, bayberry, candelilla, montan, ozokerite, ceresin, paraffin, synthetic wax and microcrystalline wax;
   B. from about 20% to about 50% of a liquid, non-toxic, non-irritating organic emollient compound having a water-solubility of from about 0.0005% to about 1% at 72° F.; and
   C. from about 30% to about 60% of a compound having antiperspirant activity selected from the group consisting of
      i. aluminium chlorhydroxide,
      ii. aluminium hydroxybromide,
      iii. mixtures of aluminum chlorhydroxide and aluminium chloride, and
      iv. antiperspirant complexes formed by
         a. co-dissolving in water
            1. one part $Al_2(OH)_{6-m}X_m$, wherein X is an anion selected from the group consisting of chloride, bromide and iodide and $m$ is a number from about 0.8 to about 1.2;
            2. n parts ZrY wherein Y is an anion selected from the group consisting of —O(OH)Cl and $OCl_2$, and where $n$ has a value of from about 0.16 to about 1.2;

3. p parts neutral amino acid selected from the group consisting of glycine, dl-tryptophane, dl-β-phenylalanine, dl-valine, dl-methionine and β-alanine, and where p has a value of from about 0.06 to about 0.53; and b. co-drying the resultant mixture at a temperature of from about 100° C. to about 230° C. to a moisture level of from about 0.5% to about 15% by weight; said compound being in impalpable powder form.

2. A stick antiperspirant composition as recited in claim 1 which additionally comprises A. from about 0% to about 25% of a low melting point waxy material which has a melting point of from about 100° F. to about 150° F. and which is selected from the group consisting fatty acids containing from about 8 to 20 carbon atoms, fatty alcohols containing from about 8 to 20 carbon atoms and glycerol monostearate; and B. from about 0% to about 10% of an inert particulate filler material selected from the group consisting of colloidal silica and a reaction product of Bentonite and dimethyldistearyl ammonium chloride.

3. A stick antiperspirant composition as recited in claim 2 wherein:

A. said high melting point wax is selected from the group consisting of white beeswax, ozokerite, ceresin and synthetic waxes;

B. said emollient is selected from the group consisting of isopropyl myristate, isopropyl palmitate, cetyl acetate and cetyl proprionate;

C. said antiperspirant compound is selected from the group consisting of aluminium chlorhydroxide, aluminium hydroxybromide, mixtures of aluminum chlorhydroxide and aluminum chloride and complexes formed from zirconium hydroxychloride, aluminium chlorhydroxide and glycine; and D. said low melting point waxy material is selected from the group consisting of cetyl alcohol, stearyl alcohol, myristyl alcohol, lauryl alcohol and glycerol monostearate.

4. A stick antiperspirant composition essentially anhydrous and comprising essentially water-insoluble materials and a water-soluble antiperspirant salt, said composition comprising A. from about 1% to about 20% of a high melting point water-insoluble wax which has a melting point of from about 150° F. to about 215° F. and which is selected from the group consisting of white beeswax, ceresin, ozokerite and synthetic waxes;

B. from about 30% to 50% of a liquid emollient selected from the group consisting of isopropyl myristate, isopropyl palmitate and the condensation product of about 14 moles of propylene oxide with one mole of butyl alcohol;

C. from about 30% to 50% of an impalpable powdered antiperspirant active compound selected from the group consisting of aluminium chlorhydroxide, aluminum hydroxybromide, mixtures of aluminium chlorhydroxide and aluminum chloride and complexes formed from zirconium hydroxychloride, aluminium chlorhydroxide and glycine; and D. from about 5% to 15% of a low melting point waxy material which has a melting point of from about 100° F. to about 150° F. and which is selected from the group consisting of cetyl alcohol, stearyl alcohol, myristyl alcohol, lauryl alcohol and glycerol monostearate.

5. A stick antiperspirant composition according to claim 4 wherein the antiperspirant active comprises from about 40% to 50% of the composition and is selected from the group consisting of complexes formed from zirconium hydroxychloride, aluminium chlorhydroxide and glycine and wherein the low melting point waxy material is cetyl alcohol.

6. A stick antiperspirant composition according to claim 5 wherein the emollient is isopropyl myristate.

7. A stick antiperspirant composition according to claim 5 wherein the emollient is the condensation product of about four moles of propylene oxide with one mole of butyl alcohol.

* * * * *